United States Patent
Finke et al.

(10) Patent No.: US 6,809,215 B2
(45) Date of Patent: Oct. 26, 2004

(54) METHOD FOR HYDROGENATION OF AROMATIC URETHANES IN THE PRESENCE OF A SUPPORTED RUTHENIUM CATALYST

(75) Inventors: Norbert Finke, Oer-Erkenschwick (DE); Ranier Lomoelder, Muenster (DE); Christian Lettmann, Coesfeld (DE); Guido Stochniol, Gelnhausen (DE)

(73) Assignee: Degussa AG, Duesseldorf (DE)

( * ) Notice: Subject to any disclaimer, the term of this patent is extended or adjusted under 35 U.S.C. 154(b) by 66 days.

(21) Appl. No.: 10/331,644
(22) Filed: Dec. 31, 2002
(65) Prior Publication Data
US 2004/0097661 A1 May 20, 2004
(30) Foreign Application Priority Data
Nov. 18, 2002 (DE) .......................... 102 53 802
(51) Int. Cl.[7] ..................... C07C 261/00; C07C 269/00; C07C 271/00
(52) U.S. Cl. ....................................... 560/115
(58) Field of Search ......................... 560/115

(56) References Cited

U.S. PATENT DOCUMENTS 4,069,240 A * 1/1978 Malz et al. ............... 560/115
5,936,126 A * 8/1999 Rühl et al. ............... 564/451
6,248,924 B1 * 6/2001 Rühl et al. ............... 564/450
6,284,917 B1 * 9/2001 Brunner et al. ........... 560/127

FOREIGN PATENT DOCUMENTS

| DE | 26 39 842 | 3/1977 |
| DE | 44 07 019 | 9/1994 |
| EP | 0 813 906 | 12/1997 |
| EP | 0 814 098 | 12/1997 |

* cited by examiner

Primary Examiner—Richard L. Raymond
Assistant Examiner—Zachary C. Tucker
(74) Attorney, Agent, or Firm—Oblon, Spivak, McClelland, Maier & Neustadt, P.C.

(57) ABSTRACT

The invention relates to a method for hydrogenation of aromatic urethanes, which contain one or more aromatic rings and one or more urethane groups bonded directly and/or indirectly to one aromatic ring or to different aromatic rings, using hydrogen in the presence of a supported catalyst, which contains ruthenium as active metal. The catalyst support of the catalyst to be used according to the invention has a BET surface ranging from larger than 30 $m^2/g$ to smaller than 70 $m^2/g$ and more than 50% of the pore volume of the catalyst support is represented by macropores with a pore diameter of larger than 50 nm and less than 50% is represented by mesopores with a pore diameter of 2 to 50 nm. The method is suitable in particular for hydrogenation of dibutyl 4,4'-methylenedicarbanilate to dibutyl 4,4'-methylenedicyclohexylcarbamate with a trans-trans isomer content of <30%, preferably of <20%, particularly preferably of 5 to 15%.

20 Claims, No Drawings

METHOD FOR HYDROGENATION OF AROMATIC URETHANES IN THE PRESENCE OF A SUPPORTED RUTHENIUM CATALYST

The invention relates to a method for hydrogenation of aromatic urethanes, which contain one or more aromatic rings and one or more urethane groups bonded directly and/or indirectly to one aromatic ring or to different aromatic rings, wherein the hydrogenation reaction is performed with hydrogen in the presence of a supported catalyst, which contains ruthenium as active metal. The catalyst to be used in the inventive method contains a catalyst support having a special combination of properties. In particular, the invention relates to a method for hydrogenation of dibutyl 4,4'-methylenedicarbanilate (hereinafter abbreviated as MDU) to dibutyl 4,4'-methylenedicyclohexylcarbamate (hereinafter abbreviated as $H_{12}MDU$) with a trans-trans isomer content of <30%, preferably of <20%, particularly preferably of 5 to 15%.

It is known that cycloaliphatic urethanes containing one or more urethane groups can be synthesized by catalytic hydrogenation of the corresponding mononuclear or polynuclear aromatic urethanes containing one or more urethane groups and possibly other substituents.

The obtained cycloaliphatic urethanes can be reacted directly with polyols to form high-quality polyurethanes that are stable to light. Rather than the cycloaliphatic urethanes, however, there are preferably used, for synthesis of polyurethanes, the corresponding cycloaliphatic isocyanates, which are accessible from the cycloaliphatic urethanes by elimination of the alcohol groups.

It is also known that, during hydrogenation of the said aromatic urethanes, there are formed aliphatic urethanes in which cis-trans isomerism is possible. In the case of hydrogenation of MDU to $H_{12}MDU$, three cis-trans isomers are possible: cis-trans-, cis-cis- and trans-trans-$H_{12}MDU$. The elimination of the alcohol groups of a mixture of $H_{12}MDU$ isomers to form bis[4-isocyanatocyclohexyl]methane (hereinafter abbreviated as $H_{12}MDI$) leads to a mixture of $H_{12}MDI$ isomers whose proportions are substantially equal to the proportions of the $H_{12}MDU$ isomers in the starting product.

The practical industrial properties of $H_{12}MDI$ are directly related to the proportion of isomers, especially to the content of the 4,4'-trans-trans isomers. In order to ensure constant product quality of the polyurethanes synthesized from the $H_{12}MDI$ and to achieve easier handling capability, it is particularly important that the $H_{12}MDI$ have the form, at room temperature, of a homogeneous liquid that does not contain solids. The temperature at which the first solid particles form in the $H_{12}MDI$ becomes lower with increasing content of the 4,4'-trans-trans isomer. Thus products with low 4,4'-trans-trans content are liquid in a broader temperature range and therefore have considerable advantages for industrial application.

As already mentioned in the foregoing, the proportion of isomers in an $H_{12}MDI$ synthesized from $H_{12}MDU$ by elimination of the alcohol groups is substantially equal to the proportion of isomers in the $H_{12}MDU$ itself. Thus, if a low 4,4'-trans-trans content is to be achieved in the $H_{12}MDI$, it will be particularly economic to produce an $H_{12}MDU$ with low 4,4'-trans-trans content during hydrogenation of the MDU, so that it can then be directly further processed to an $H_{12}MDI$ with correspondingly low 4,4'-trans-trans content.

As follows from the documents cited hereinafter, the hydrogenation of aromatic urethanes to the corresponding cycloaliphatic urethanes is achieved in some cases by using supported catalysts.

U.S. Pat. No. 5,360,934 teaches the method of the class in question, but uses a supported catalyst containing rhodium for the purpose. Ruthenium can also be present as the active metal. According to the teaching of that document, the catalyst activity depends considerably on the modification of the aluminum oxide used as support. Apparently catalysts containing delta, theta and kappa aluminum oxide are more active as support material than a catalyst containing commercial gamma aluminum oxide as support material.

In the method according to European Patent 0813906, organic compounds can be hydrogenated using a supported ruthenium catalyst. These compounds also include aromatic compounds in which at least one functional group is bonded to an aromatic nucleus. In addition to ruthenium, the catalyst can also contain other metals from the subgroups of Groups I, VII or VIII of the Periodic Table. The support material has a BET surface of at most 30 $m^2/g$ and an average pore diameter of at least 50 nm. The catalyst used here is also characterized by a ratio of surface area of the active metal to surface area of the catalyst support of smaller than 0.05. The macroporous support materials with an average pore diameter of preferably 500 nm to approximately 50 $\mu m$ are mainly aluminum oxide and zirconium oxide. Details on the hydrogenation of MDU to HMDU cannot be inferred from that document. In particular, there is described the hydrogenation of substituted aromatic compounds, in which either at least one hydroxy group or one amino group is bonded to an aromatic nucleus. In contrast, the object set by the inventors of the present application was to convert substituted aromatic urethanes to cycloaliphatic urethanes with low 4,4'-trans-trans content.

A method similar to that of European Patent 0813906 is taught in European Patent 0814098: In this case there are used, as support material for the supported ruthenium hydrogenation catalyst, materials in which 10 to 50% of the pore volume is represented by macropores with a pore diameter ranging from 50 to 10,000 nm and 50 to 90% is represented by mesopores with a pore diameter ranging from 2 to 50 nm. The BET surface of the support is specified as 50 to 500 $m^2/g$, especially 200 to 350 $m^2/g$. The ratio of the surface area of the active metal to that of the support is supposed to be smaller than 0.3, especially smaller than 0.1. Particulars on the activity of such catalysts and on the proportions of isomers during the hydrogenation of MDU to $H_{12}MDU$ cannot be inferred from that document.

From European Patent 0653243 there are known catalysts suitable for hydrogenation of aromatic compounds. The catalysts listed therein are systems formed by introduction of the dissolved active component into an organic polymer. This mixture must be mixed in turn with a support material, then molded and heat-treated. This method of producing the catalyst is relatively complex, since numerous individual partial steps must be considered. In total, these steps are cost-intensive, since several chemical additives are necessary. Moreover, the active component becomes homogeneously mixed with the support compound, and so only part of this component is available for catalytic reaction.

German Unexamined Application 2639842 describes a method for synthesis of cycloaliphatic urethanes by hydrogenation of aromatic urethanes. Transition metals of Group VIII of the Periodic Table are used as hydrogenation catalysts, rhodium being particularly preferred. Among other reactions, the hydrogenation of dimethyl 4,4'-methylenedicarbanilate to dimethyl 4,4'-methylenedicyclohexylcarbamate is also described. The hydrogenation reaction is performed in an inert solvent, preferably an aliphatic alcohol. A disadvantage of this method is that the catalysts used rapidly lose activity and can be only partly regenerated by rinsing with sulfuric acid, methanol and 2-propanol. Moreover, no particulars are given regarding the 4,4'-trans-trans content in the product and, moreover, no indication of any kind can be found that this is of importance.

In German Unexamined Application 4407019 there is described a method for hydrogenation of aromatic urethanes in an inert solvent with metals of Group VIII of the Periodic Table or compounds thereof as hydrogenation catalysts, ruthenium being particularly preferred. The synthesis of $H_{12}$MDI from MDI is cited as an example. This example describes the hydrogenation of dimethyl 4,4'-methylenedicarbanilate to dimethyl 4,4'-methylenedicyclohexylcarbamate. Particulars on the 4,4'-trans-trans content of the product cannot be inferred from the document. Supported catalysts are mentioned only in passing.

From European Patent 0023649 there is known a method for synthesis of aliphatic isocyanates from aromatic isocyanates, characterized in that an aromatic isocyanate is first reacted with a lactam and, in a subsequent step, the nucleus of the lactam-blocked isocyanate is hydrogenated with a rhodium catalyst. The lactam is thermally eliminated in order to obtain the free aliphatic isocyanate. A disadvantage is that the lactam-blocked aromatic isocyanates already dissociate back to isocyanate and lactam at relatively low temperatures, thus leading to losses of yield and to deactivation of the catalyst. To ensure low reaction temperatures, there are therefore used exclusively rhodium-based catalysts, which are very expensive because of the fact that the price of rhodium is relatively high compared to that of ruthenium. From the examples presented in European Patent 0023649, it follows that a product with a 4,4'-trans-trans isomer content of 32.1% results during the conversion of MDI to $H_{12}$MDI. According to the description, and as expected, this product is no longer completely liquid at room temperature, but contains crystals.

European Patent 0268856 teaches a method for synthesis of aralkylurethanes, monourethanes and diurethanes by acid-catalyzed addition of formaldehyde and carbamic acid esters to aromatics. The products synthesized in this way can either be dissociated directly to aromatic isocyanates or their nuclei can be hydrogenated first, before they are dissociated to liberate the aliphatic isocyanates. No indications can be found as to the distribution of cis-trans-isomers in the products. In particular, a method for synthesis of $H_{12}$MDU cannot be inferred from the document.

The object of the present invention is to provide a method for hydrogenation of aromatic urethanes in the presence of a ruthenium-containing supported catalyst, with which the desired cycloaliphatic urethanes can be obtained with high selectivity. Another object of the invention is to provide a method for synthesis of $H_{12}$MDU by catalytic hydrogenation of MDU, wherein the 4,4'-trans-trans isomer content of the $H_{12}$DMU is smaller than 30%, preferably smaller than 20%, particularly preferably 5 to 15%. A further object is to ensure that the 4,4'-trans-trans content remains low despite high conversion. According to yet another object, the catalyst used in the method should have a long useful life and the distribution of isomers should remain substantially unchanged even after prolonged operating time.

The subject matter of the invention is a method for hydrogenation of aromatic urethanes, which contain one or more aromatic rings and one or more urethane groups bonded directly and/or indirectly to one aromatic ring or to different aromatic rings, by reacting the aromatic urethane with hydrogen in the presence of a supported catalyst, which contains as active metal, applied on a support, ruthenium alone or together with at least one metal of the subgroups of Groups I, VII or VIII of the Periodic Table, the proportion of active metal being 0.01 to 20 wt % relative to the supported catalyst, and wherein the catalyst support has a BET surface ranging from larger than 30 $m^2/g$ to smaller than 70 $m^2/g$ and more than 50% of the pore volume of the catalyst support is represented by macropores with a pore diameter of larger than 50 nm and less than 50% is represented by mesopores with a pore diameter of 2 to 50 nm, The dependent claims relate to preferred embodiments of the inventive method.

As regards the prior art evaluated thoroughly hereinabove, especially European Patent 0814098, it was surprising that a catalyst support with a specific surface ranging from larger than 30 $m^2/g$ to smaller than 70 $m^2/g$ is particularly active in the method of the class in question when more than 50% of the pore volume is represented by macropores and less than 50% of the pore volume is represented by mesopores. Thus it is not the BET surface alone or the pore distribution alone that is important, but instead the combination of these two features. Finally, the catalyst to be used in the method according to the present invention differs in principle from the catalyst cited in European Patent 0813906 A2 by the fact that the catalyst support in the prior art method is indeed macroporous, but the BET surface is at most 30 $m^2/g$ and preferably at most 15 $m^2/g$. The ratio of the surface area of the active metal to that of the catalyst support ranges from 0.01 to 0.5, especially from 0.03 to 0.3. Surprisingly, even a small ratio, on the order of 0.03 to 0.06, of the surface area of the active metal, determined by CO chemisorption, to that of the catalyst support, determined by the BET method, leads to high catalyst activity under mild conditions for the catalyst to be used according to the invention.

It was surprisingly found that hydrogenation products with low trans-trans-isomer proportions of smaller than 30% are obtained by the inventive method in combination with the catalysts used according to the invention. In particular, the method is also suitable for synthesis of hydrogenation products with a trans-trans isomer content of smaller than 20%, especially of 5 to 15%, from bridged binuclear starting products, such as mentioned in the next section.

The method is suitable in particular for hydrogenation of dibutyl 4,4'-methylenedicarbanilate to dibutyl 4,4'-methylenedicyclohexylcarbamate with a trans-trans isomer content of <30%, preferably of <20%, particularly preferably of 5 to 15%.

Aromatic Urethanes:

By means of the inventive method, it is possible to hydrogenate aromatic urethanes of any kind to the corresponding cycloaliphatic compounds. These aromatic compounds can be mononuclear or polynuclear aromatic compounds. Preferably the aromatic compounds are mononuclear and binuclear aromatic urethanes or diurethanes or triurethanes. The aromatic urethanes can be substituted on the aromatic nucleus or nuclei or/and on the urethane group, for example by one or more alkyl and/or alkoxy groups, preferably $C_{1-20}$ alkyl and/or $C_{1-20}$ alkoxy groups. Particularly preferred substituents are $C_{1-10}$ alkyl groups, especially methyl, ethyl, propyl, isopropyl, butyl, isobutyl and tert-butyl groups: among the alkoxy groups there are preferred the $C_{1-8}$ alkoxy groups, especially methoxy, ethoxy, propoxy and butoxy. The aromatic nucleus or nuclei as well as the alkyl and alkoxy groups can be substituted if necessary by halogen atoms, especially fluorine atoms, or can have other suitable inert substituents or substituents that are amenable to hydrogenation.

The aromatic urethane can also have several aromatic nuclei linked by a divalent hydrocarbon group, such as a methylene group or ethylene group, and one or both aromatic nuclei can have a further urethane group and/or a $C_1$ to $C_3$ alkyl or alkoxy group. The linking group can have one or more alkyl substituents, especially $C_{1-20}$ alkyl groups, preferably one or more methyl, ethyl, n-propyl, isopropyl, n-butyl, sec-butyl or tert-butyl groups.

Particularly preferred aromatic urethanes are the compounds listed hereinafter and described by formulas:

dialkyl 4,4'-methylenedicarbanilate, dialkyl 2,4'-methylenedicarbanilate, dialkyl 2,2'-methylenedicarbanilate and polynuclear methylene-bridged alkyl carbanilates (PMDU) as well as mixtures thereof,

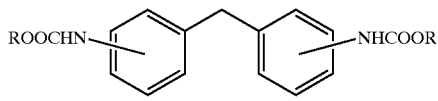

R = $C_1$–$C_6$ alkyl, preferably n-butyl

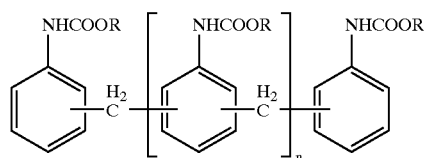

PMDU, R = $C_1$–$C_6$ alkyl, preferably n-butyl, n = 1 to 10 dialkyl 4,4'-methylene-3,3'-dicarbanilate, dialkyl 2,4'-methylene-3,3'-dicarbanilate, dialkyl 2,2'-methylene-3,3'-dicarbanilate as well as mixtures thereof,

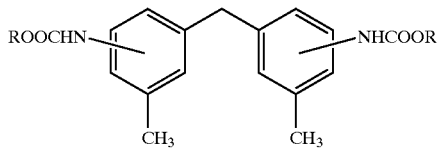

R = $C_1$–$C_6$ alkyl, preferably n-butyl dialkyl 1,2-phenyldicarbamate, dialkyl 1,3-phenyldicarbamate and dialkyl 1,4-phenyldicarbamate as well as mixtures thereof,

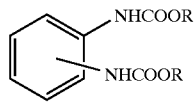

R = $C_1$–$C_6$ alkyl, preferably n-butyl dialkyl 2,4-toluenedicarbamate, dialkyl 2,6-toluenedicarbamate as well as mixtures thereof

R = $C_1$–$C_6$ alkyl, preferably n-butyl dialkyl 1,6-naphthalenedicarbamate,

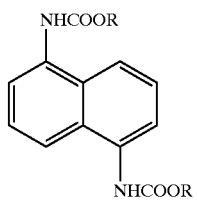

R = $C_1$–$C_6$ alkyl, preferably n-butyl the urethanes corresponding to the compounds abbreviated as MXDI and TMXDI,

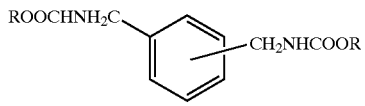

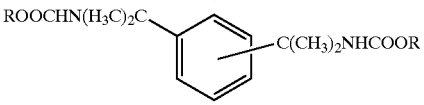

R = alkyl, preferably n-butyl

Preferred compounds are dialkyl 4,4'-($C_1$ to $C_4$)alkanedicarbanilate and/or a 2,4'-isomer and/or 2,2'-isomer or mixtures thereof, particularly preferably dibutyl 4,4'-methylenedicarbanilate or an isomer or a mixture (MDU). In particular, dibutyl 4,4'-methylenedicarbanilate is hydrogenated to dibutyl 4,4'-methylenedicyclohexylcarbamate with a trans-trans isomer content of <30%, preferably of <20%, particularly preferably of 5 to 15%.

For the purposes of the process according to the invention, preference is given to using a starting material which does not impair the onstream time of the catalyst. It has proven advantageous when no phosphorus, sulfur and/or chlorine compounds are present in the starting material.

Catalysts:

The supported catalysts to be used according to the invention can be synthesized industrially by application of ruthenium and if necessary of at least one metal of the subgroups of Groups I, VII or VIII on a suitable support. Application can be achieved by immersion of the support in aqueous solutions of metal salt, such as solutions of ruthenium salt, by spraying appropriate solutions of metal salt onto the support or by other suitable methods. Suitable salts for preparation of the solutions of ruthenium salts as well as solutions of metal salts of elements of the subgroups of Groups I, VII or VIII include the nitrates, nitrosylnitrates, halides, carbonates, carboxylates, acetylacetonates, chlorine complexes, nitro complexes or amine complexes of the corresponding metals; nitrates and nitrosylnitrates are preferred.

In catalysts that contain further metals applied on the support in addition to ruthenium, the metal salts or solutions of metal salts can be applied simultaneously or consecutively.

The supports coated or impregnated with a ruthenium salt or additionally with further solutions of metal salts are dried, preferably at temperatures of between 100 and 150° C., and optionally are calcined at temperatures of between 200 and 600° C. Thereafter the coated supports are activated by treating the coated supports in a gas stream containing free hydrogen at temperatures of between 30 and 600° C., preferably of between 150 and 400° C. The gas stream is preferably composed of 50 to 100 vol % of $H_2$ and 0 to 50 vol % of $N_2$.

If one or more other metals of the subgroups of Groups I, VII or VIII is applied onto the supports in addition to ruthenium, and if such application takes place consecutively, the support can be dried at temperatures of between 100 and 150° C. after each application or impregnation and optionally calcined at temperatures of between 200 and 600° C. The sequence in which the solutions of metal salts is applied can be chosen as desired.

According to a preferred embodiment, the support is coated by spraying it with a solution of metal salt at elevated temperature, especially above 50° C. and particularly preferably at 80 to 150° C., so that the solvent is already evaporated at least partly during the coating operation and the depth of penetration of the catalytically effective metals is limited. Preferably the depth of penetration ranges from 5 to 250 μm, especially from 10 to 150 μm and particularly preferably from 50 to 120 μm.

The solution of ruthenium salt and if necessary solutions of further metal salts are applied in such a quantity on the support or supports that the proportion of ruthenium and if necessary of other metals of the subgroups of Groups I, VII or VIII applied on the support corresponds to 0.01 to 20 wt % relative to the total weight of the catalyst. Preferably the quantity of active metals corresponds to 0.2 to 15 wt %, especially to about 0.2 to 3 wt %, the ruthenium content exceeding the content of the other metals by an appropriate value.

Support Materials:

The support materials of the catalysts to be used according to the invention have a specific BET surface (determined according to DIN 66131, using $N_2$) ranging from larger than 30 m²/g to smaller than 70 m²/g.

The support contains macropores with a pore diameter of larger than 50 nm. The diameter of the macropores ranges in particular from 50 to 50,000 nm, but frequently falls within the range of 50 to 10,000 nm. If the support also contains mesopores, pores in the size range from 2 to 50 nm are to be understood thereby. At least 50% of the pore volume is represented by macropores and less than 50% by mesopores. Preferred supports contain macropores in a proportion of 55 to 85% of the pore volume, and 15 to 45% of the pore volume corresponds to mesopores. In particularly preferred supports, mesopores account for about 25 to 45% of the pore volume and macropores for the rest of the pore volume. Micropores with a pore diameter of smaller than 2 nm, if present at all, represent only a proportion of less than 10% of the pore volume, especially of less than 1%.

The support can comprise uniform or mixed modifications, and so the pore distribution can be monomodal, bimodal or trimodal.

In principle, all known support materials for hydrogenation catalysts can be used, provided they have the BET surface, pore size and pore distribution according to the claims. Suitable supports can be oxides, silicates and nitrides, with single-phase or multiphase crystalline structure, with radiographically amorphous structure or with mixed structure.

The supports can be further modified in known manner by means of alkali metal and or alkaline earth compounds and/or with metals of the lanthanide series.

Examples of supports include oxides from the series comprising $Al_2O_3$, $TiO_2$, $ZrO_2$, $SiO_2$, MgO and ZnO, as well as mixed oxides, including spinels such as $MgAl_2O_4$. Aluminosilicates and active charcoal are also suitable, provided such supports have the combination of properties according to the claims. Particularly preferred oxides are $Al_2O_3$ and $TiO_2$.

Hydrogenation Conditions:

The hydrogenation step is carried out at a temperature ranging from 20 to 250° C., especially below 200° C., and an effective $H_2$ partial pressure ranging from about 1 to 30 MPa, preferably lower than 15 MPa, in a suspension or fixed-bed hydrogenation reactor in continuous or batchwise operation. The activity of the inventive catalysts ensures that the hydrogenation step can be carried out under mild conditions, especially at a temperature ranging from 50 to 150° C., especially 70 to 120° C. and an $H_2$ pressure ranging from 3 to 15 MPa, thus allowing the use of industrially less complex reactors and improving the economy of the method.

A further economic advantage resulting from the mild hydrogenation conditions is an increased total yield of the method. This is due mainly to the fact that dissociation of the urethane back to isocyanate and alcohol becomes more pronounced with rising temperature. Subsequent hydrogenation of the unprotected isocyanate group leads to formation of undesired secondary products, which must be separated from the product and thus cause a loss of yield.

The hydrogenation step can be performed in the presence or absence of a suitable solvent. Preferably a solvent is present, specifically in a proportion of about 10 to 90 wt % relative to the solution of the aromatic urethane to be hydrogenated.

Examples of suitable solvents include primary, secondary and tertiary monohydric or polyhydric alcohols, such as methanol, ethanol, n-propanol, i-propanol, n-butanol, sec-butanol, tert-butanol, ethylene glycol, ethylene glycol mono ($C_1$ to $C_4$)alkyl ether, straight-chain ethers such as ethylene glycol di($C_1$ to $C_3$)alkyl ethers, cyclic ethers such as tetrahydrofuran and dioxane, alkanes such as n-alkanes and iso-alkanes with 4 to 12 C atoms, such as n-pentane, n-hexane and isooctane, and cyclic alkanes such as cyclohexane and decalin.

The hydrogenation product itself, or in other words a cycloaliphatic urethane, can also be a solvent.

In a preferred embodiment of the method, there is used a mixture of two or more solvents, composed of alcohols and ethers, in which the alcohol corresponds in particular to the alcohol group contained in the urethane, preferably n-butanol. The preferred ether is THF. It has been surprisingly found that not only does the alcohol addition lead to an increase of hydrogenation selectivity, which on the basis of the law of mass action is due to the expected decrease of dissociation of the urethane back to alcohol and isocyanate, but also the activity of the catalyst and thus the space-time yield of the overall process are considerably increased. The alcohol content of the solvent mixture varies from 0.1 to 99.9 wt %, preferably lower than 50%, particularly preferably from 5 to 30 wt %.

A fixed-bed reactor is preferred for continuous hydrogenation. The fixed-bed reactor can be operated as a bubble reactor, although a trickling-bed procedure is preferred. A trickling-bed reactor preferably has an LHSV value ranging from 0.1 to 5 h$^{-1}$ (=liters of reaction solution per liter of fixed-bed catalyst per hour). According to a particularly preferred embodiment of the inventive method, there is used a tube reactor operated by the trickling-bed procedure.

Further subject matter of the present invention is the use, for hydrogenation of aromatic urethanes, which contain one or more aromatic rings and one or more urethane groups bonded directly and/or indirectly to one aromatic ring or to different aromatic rings, of a supported catalyst, which contains as active metal, applied on a support, ruthenium alone or together with at least one metal of the subgroups of Groups I, VII or VIII of the Periodic Table, the proportion of active metal being 0.01 to 20 wt % relative to the supported catalyst, wherein the catalyst support has a BET surface ranging from larger than 30 $m^2/g$ to smaller than 70 $m^2/g$ and more than 50% of the pore volume of the catalyst support is represented by macropores with a pore diameter of larger than 50 nm and less than 50% is represented by mesopores with a pore diameter of 2 to 50 nm. Preferably the proportion of ruthenium exceeds the proportion of the other active metals. Preferably the catalyst contains 0.2 to 3 wt % of active metal and, in particular at least 90% thereof is ruthenium.

EXAMPLES
Preparation of the Catalyst

Example 1

Aluminum oxide molded bodies (extrudate, d=3 mm) with a BET surface of about 33 $m^2/g$ and a bimodal pore distribution with a pore volume of 0.41 ml/g, wherein substantially no pores with a diameter of 2 to 50 nm were observed but 100% of the pore volume was represented by macropores with a diameter in the range of 50 to 10,000 nm, were coated with an aqueous ruthenium(III) nitrate solution at about 90 to 100° C., by spraying the catalyst solution onto the support material while it was being kept in motion, water being evaporated simultaneously. The catalyst solution had a concentration of 5% of metal relative to the weight of the solution. The support coated in this way was heated at a temperature of 120 to 180° C. and then reduced for 4 hours at 200° C. using a mixture of 50% $H_2$ and 50% $N_2$. The catalyst prepared in this way had a content of 3 wt % of ruthenium relative to the total weight of the catalyst. The depth of penetration of the ruthenium was 70 to 90 μm. The ratio of the ruthenium surface area, determined by CO chemisorption, to the surface area of the uncoated support material, determined by the BET method, was about 0.05. The aluminum oxide molded bodies were composed substantially of alpha and gamma $Al_2O_3$ (about 18 wt % of $SiO_2$ and about 2 wt % of alkali metal and alkaline earth oxides, $Fe_2O_3$ and $TiO_2$).

Example 2

Aluminum oxide molded bodies (extrudate, d=3 mm) with composition similar to that of the support of Example 1 and with a BET surface of about 32 $m^2/g$, trimodal pore distribution and a pore volume of 0.58 ml/g, were impregnated in a manner analogous to that of Example 1. Of the pore volume of the support material, 31% resulted from pores with a diameter of 2 to 50 nm, 44% from pores with a diameter of 50 to 10,000 nm and 25% from pores with a diameter of larger than 10,000 nm up to 5 μm. The catalyst prepared in this way had a ruthenium content of 3 wt %, as in Example 1, and the depth of penetration was 70 to 90 μm.

Example 3

Aluminum oxide molded bodies (extrudate, d=3 mm) with a surface of about 54 $m^2/g$ exhibited a trimodal pore distribution and had a pore volume of 0.77 ml/g. Of the pore volume, 40% resulted from pores with a diameter of 2 to 50 nm and 60% from pores with a diameter of 50 to 10,000 nm. Impregnation of the support as well as calcination and reduction of the catalyst were performed in the same way as in Example 1. The catalyst prepared in this way contained 3 wt % of ruthenium relative to the total weight of the catalyst. The depth of penetration was 70 to 90 nm. The aluminum oxide molded bodies used contained the alpha, theta and gamma modifications of $Al_2O_3$.

Example 4

Aluminum oxide molded bodies in the form of spherical pellets having a size of 2 to 4 mm with a BET surface of about 35 $m^2/g$ exhibited, in a monomodal pore distribution, a pore volume of 0.5 ml/g. Of the pore volume, 42% was represented by mesopores (2 to 50 nm) and 58% was represented by macropores (50 to 10,000 nm). The support material contained the theta and gamma $Al_2O_3$ modifications. Impregnation, calcination and reduction were performed in the same way as in Example 1. The supported ruthenium catalyst prepared in this way contained 3 wt % of ruthenium relative to the total weight of the catalyst. The depth of penetration of the ruthenium was 80 to 120 μm.

Comparison Example 1

Titanium dioxide molded bodies (extrudate, d=2 mm) comprising substantially a mixture of rutile and anatase with a BET surface of 45 $m^2/g$ exhibited, in a monomodal pore distribution, a pore volume of 0.35 ml/g. 100% of the pore volume was represented by mesopores (2 to 50 nm). The molded bodies were impregnated in the same way as in Example 1, but drying was performed at 150 to 160° C. and the subsequent reduction took place at 180° C. for 4 hours. The catalyst prepared in this way contained 3 wt % of ruthenium relative to the total weight of the catalyst. The depth of penetration was 90 to 120 μm.

Comparison Example 2

Aluminum oxide molded bodies (extrudate, d=1.2 nm) comprising substantially gamma $Al_2O_3$ with a BET surface of 220 $m^2$ g had a pore volume of 0.65 ml/g, 95% of the pore volume being represented by mesopores (2 to 50 nm) and 5% of the pore volume being represented by macropores (50 to 10,000 nm. The support was impregnated with an aqueous ruthenium(III) nitrate solution at room temperature. The catalyst solution had a concentration of 5% of metal relative to the weight of the solution. The impregnated support was heated at a temperature of 150 to 160° C. and then reduced for 4 hours at 180° C. using a mixture of 50% $H_2$ and 50% $N_2$. The catalyst prepared in this way had a content of 5 wt % of ruthenium relative to the total weight of the catalyst. The depth of penetration was as much as 600 μm.

Performance of the Hydrogenation Reaction

Example 5

Preparation of an MDU Solution Containing 10 wt % of MDU, 10 wt % of n-butanol and 80 wt % of THF 2400 g of THF (33.3 mol) and 300 g of n-BuOH (4.05 mol) were placed in a 5-liter three-necked flask with stirring apparatus and heatable dropping funnel. The solution was heated to boiling (about 70° C.) and then 188.4 g of MDI (0.75 mol) was smoothly added dropwise in molten form. The mixture was maintained under reflux until completion of the reaction (about 6 hours). The completeness of the reaction was checked by determination of the NCO number and by IR spectroscopy.

When a different MDU and/or n-butane content was desired, the quantities of starting materials were adapted accordingly.

Example 6
Hydrogenation of MDU Solutions with Different n-butanol Contents in the Autoclave at 100° C.

This example is intended to illustrate the influence of n-butanol on the catalyst activity.

By analogy with Example 5, three 10 wt % MDU solutions were prepared with different n-butanol contents (0, 10 and 20 wt % in the final solution, MDI from the Aldrich Co.). These solutions were hydrogenated at 100° C. and 80 bar in a 1-liter laboratory autoclave containing a catalyst basket. In each case there were used 600 g of MDU solution and 48.3 g of inventive catalyst. After 5 hours a sample was removed from the reactor and analyzed by means of HPLC/CLND, HPLC/MS and GC-PTV-MS. The result is presented in Table 1. It can be clearly seen that, with increasing n-butanol content in the reaction mixture, fewer hydrogenable intermediate products are present in the end product after 5 hours, while the $H_{12}$MDU content is higher. This is equivalent to a distinct increase of the rate of reaction. According to the invention the content of the 4,4'-trans-trans isomer is low, with a value of about 8%.

TABLE 1

Result of hydrogenation of MDU solution with different n-butanol contents. Hydrogenation conditions: 100° C., 80 bar. All values in wt %.

|  | Reaction mixture No. | | |
| --- | --- | --- | --- |
|  | 1 | 2 | 3 |
| Starting mixture composition | | | |
| MDU | 10 | 10 | 10 |
| THF | 90 | 80 | 70 |
| n-Butanol | 0 | 10 | 20 |
| Product composition[1] | | | |
| MDU | 6.8 | 0 | 0 |
| Hydrogenable Intermediate products[2] | 54.9 | 15 | 3.3 |
| $H_{12}$MDU | 36.4 | 81.9 | 92.3 |
| Secondary products | 1.9 | 3.1 | 4.4 |
| 4,4'-Trans-trans content[3] | 7 | 8 | 8 |

[1]After subtraction of n-butanol and THF.
[2]Only those that can be further hydrogenated to $H_{12}$MDU in the further course of the reaction.
[3]Proportion of trans-trans-$H_{12}$MDU relative to the sum of the contents of all $H_{12}$MDU isomers.

Example 7
Hydrogenation of MDU Solutions with Different n-butanol Contents in the Autoclave at 120 ° C.

This example is intended to illustrate the positive influence of n-butanol on the selectivity.

By analogy with Example 5, three 10 wt % MDU solutions were prepared with different n-butanol contents (0, 10 and 20 wt % in the final solution, MDI from the Aldrich Co.). These solutions were hydrogenated at 120° C. and 80 bar in a I-liter laboratory autoclave containing a catalyst basket. In each case there were used 600 g of MDU solution and 48.3 g of inventive catalyst. After 4 hours a sample was removed from the reactor and analyzed by means of HPLC/CLND, HPLC/MS and GC-PTV-MS. The result is presented in Table 2. In all experiments, hydrogenable intermediate product is no longer detectable after 4 hours. It can be clearly seen that, with increasing n-butanol content in the reaction mixture, the proportion of secondary product decreases. This is equivalent to a distinct increase of the selectivity. According to the invention the content of the 4,4'-trans-trans isomer is low, with a value of about 8%.

TABLE 2

Result of hydrogenation of MDU solution with different n-butanol contents. Hydrogenation conditions: 120° C., 80 bar. All values in wt %.

|  | Reaction mixture No. | | |
| --- | --- | --- | --- |
|  | 1 | 2 | 3 |
| Starting mixture composition | | | |
| MDU | 10 | 10 | 10 |
| THF | 90 | 80 | 70 |
| n-Butanol | 0 | 10 | 20 |
| Product composition[1] | | | |
| MDU | 0 | 0 | 0 |
| Hydrogenable Intermediate products[2] | 0 | 0 | 0 |
| $H_{12}$MDU | 92 | 93.5 | 94.8 |
| Secondary products | 8 | 6.5 | 5.2 |
| 4,4'-Trans-trans content[3] | 8 | 7 | 7 |

[1]After subtraction of n-butanol and THF.
[2]Only those that can be further hydrogenated to $H_{12}$MDU in the further course of the reaction.
[3]Proportion of trans-trans-$H_{12}$MDU relative to the sum of the contents of all $H_{12}$MDU isomers.

Example 8
Hydrogenation of MDU Solutions with Different n-butanol Contents in the Trickling-bed Reactor at 100° C.

By analogy with Example 5, three 10 wt % MDU solutions were prepared with different n-butanol contents (0, 5 and 10 wt % in the final solution). These solutions were hydrogenated at 100° C. and 80 bar in a trickling-bed reactor packed with 14.5 g of inventive catalyst. The removed samples were analyzed by means of HPLC/CLND, HPLC/MS and GC-PTV-MS. The result is presented in Table 3.

It can be clearly seen that, with increasing n-butanol content in the reaction mixture, the proportion of secondary product decreases. This is equivalent to a distinct increase of the selectivity. At the same time the proportion of unreacted MDU decreased. According to the invention the content of the 4,4'-trans-trans isomer is low, with a value of about 8.9 to 9.8%.

TABLE 3

Result of continuous hydrogenation of MDU solution with different n-butanol contents. Hydrogenation conditions: 100° C., 80 bar. All values in wt %.

|  | Reaction mixture No. | | |
| --- | --- | --- | --- |
|  | 1 | 2 | 3 |
| Starting mixture composition | | | |
| MDU | 10 | 15 | 10 |
| THF | 90 | 80 | 80 |
| n-Butanol | 0 | 5 | 10 |

TABLE 3-continued

Result of continuous hydrogenation of MDU solution
with different n-butanol contents.
Hydrogenation conditions: 100° C., 80 bar.
All values in wt %.

| | Reaction mixture No. | | |
|---|---|---|---|
| | 1 | 2 | 3 |
| Product composition[1] | | | |
| MDU | 8.6 | 0 | 0 |
| Hydrogenable Intermediate products[2] | 47.6 | 0.4 | 0 |
| $H_{12}$MDU | 39.1 | 95.7 | 98.1 |
| Secondary products | 4.6 | 3.9 | 2.0 |
| 4,4'-Trans-trans content[3] | 9.6 | 8.9 | 9.8 |

[1]After subtraction of n-butanol and THF.
[2]Only those that can be further hydrogenated to $H_{12}$MDU in the further course of the reaction 46680046.
[3]Proportion of trans-trans-$H_{12}$MDU relative to the sum of the contents of all $H_{12}$MDU isomers.

We claim:

1. A method for hydrogenation of an aromatic urethane, which contain one or more aromatic rings and one or more urethane groups bonded directly and/or indirectly to one aromatic ring or to different aromatic rings, by reacting the aromatic urethane with hydrogen in the presence of a supported catalyst, which contains as active metal, applied on a support, ruthenium alone or together with at least one metal of the subgroups of Groups I, VII or VIII of the Periodic Table, the proportion of active metal being 0.01 to 20 wt % relative to the supported catalyst, and wherein the catalyst support has a BET surface ranging from larger than 30 m$^2$/g to smaller than 70 m$^2$/g and more than 50% of the pore volume of the catalyst support is represented by macropores with a pore diameter of larger than 50 nm and less than 50% is represented by mesopores with a pore diameter of 2 to 50 nm.

2. The method according to claim 1, characterized in that the active metal applied on the catalyst has a depth of penetration into the support ranging from 20 to 500 μm.

3. The method according to claim 1, characterized in that the ratio of the surface area of the active metal, determined by CO pulse chemisorption, to that of the catalyst support, determined by the BET method, is larger than 0.01.

4. The method according to claim 1, characterized in that the support material is selected from the group consisting of crystalline and amorphous oxides and crystalline and amorphous silicates.

5. The method according to claim 1, characterized in that the catalyst support has a BET surface ranging from 32 to 67 m$^2$/g, a depth of penetration of the active metal into the support ranges from 50 to 200 μm, and the Ru content ranges from 0.2 to 3 wt % relative to the catalyst, and at least 55% of the pore volume of the catalyst support is represented by macropores and less than 45% is represented by mesopores.

6. The method according to claim 1, characterized in that the hydrogenation step is carried out in a suspension or fixed-bed hydrogenation reactor in continuous or batchwise operation, at a temperature ranging from 20 to 250° C., and a hydrogen partial pressure ranging from 1 to 30 MPa.

7. The method according to claim 1, characterized in that the hydrogenation step is carried out in a fixed-bed reactor.

8. The method according to claim 1, characterized in that there is used a supported catalyst whose active metal, ruthenium, was applied onto a support by spraying the support with a dilute ruthenium solution, at a temperature of at least 80° C., with subsequent heat treatment and activation of the catalyst by reduction in a hydrogen-containing gas.

9. The method according to claim 1, characterized in that the compounds hydrogenerated are selected from dialkyl 4,4'-methylenedicarbanilate, dialkyl 2,4'-methylenedicarbanilate, dialkyl 2,2'-methylenedicarbanilate and polynuclear methylene-bridged alkyl carbanilates (PMDU) as well as mixtures thereof,

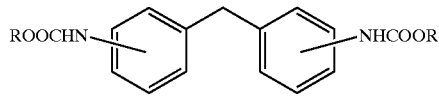

R = $C_1$–$C_6$ alkyl,

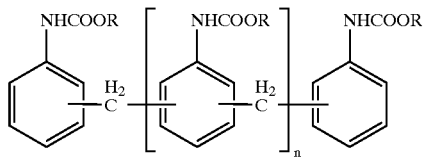

PMDU, R = $C_1$–$C_6$ alkyl, n = 1 to 10 dialkyl 4,4'-methylene-3,3'-dicarbanilate, dialkyl 2,4'-methylene-3,3'-dicarbanilate, dialkyl 2,2'-methylene-3,3'-dicarbanilate as well as mixtures thereof,

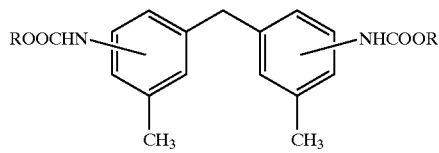

R = $C_1$–$C_6$ alkyl, dialkyl 1,2-phenyldicarbamate, dialkyl 1,3-phenyldicarbamate and dialkyl 1,4-phenyldicarbamate as well as mixtures thereof,

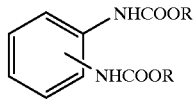

R = $C_1$–$C_6$ alkyl, dialkyl 2,4-toluenedicarbamate, dialkyl 2,6-toluenedicarbamate as well as mixtures thereof,

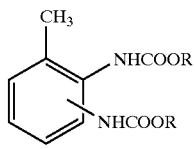

R = $C_1$–$C_6$ alkyl, dialkyl 1,6-naphthalenedicarbamate,

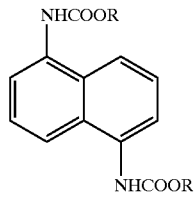

R = $C_1$–$C_6$ alkyl, and the urethanes corresponding to the compounds abbreviated as MXDI and TMXDI,

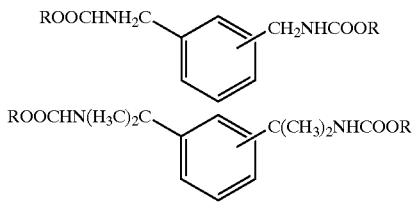

R = alkyl.

10. The method according to claim 1, characterized in that there is hydrogenated a dialkyl 4,4'-($C_1$ to $C_4$)alkanedicarbanilate and/or a 2,4'-isomer and/or 2,2-isomer or mixtures thereof.

11. The method according to claim 10, characterized in that there is hydrogenated a dibutyl 4,4'-methylenedicarbanilate or an isomer or a mixture thereof.

12. The method according to claim 1, characterized in that hydrogenation products with a trans-trans isomer content of <30% are synthesized from bridged binuclear starting products.

13. The method according to claim 1, for hydrogenation of dibutyl 4,4'-methylenedicarbanilate to dibutyl 4,4'-methylenedicyclohexylcarbamate with a trans-trans isomer content of <30%.

14. The method according to claim 1, characterized in that the hydrogenation step is performed in a solvent or solvent mixture of alcohols and/or ethers.

15. The method according to claim 14, characterized in that the alcohols correspond to the alcohol group of the urethane.

16. The method according to claim 14, characterized in that the alcohols and/or ethers include n-butanol and tetrahydrofuran.

17. The method according to claim 1, characterized in that the active metal applied on the catalyst has a depth of penetration into the support ranging from 25 to 250 µm.

18. The method according to claim 1, characterized in that the ratio of the surface area of the active metal, determined by CO pulse chemisorption, to that of the catalyst support, determined by the BET method, is in a range of from 0.03 to 0.3.

19. The method according to claim 1, characterized in that the support material is selected from the group consisting of $Al_2O_3$, $SiO_2$, $TiO_2$, $ZrO_2$, MgO, ZnO and aluminosilicates.

20. The method according to claim 1, characterized in that the aromatic urethane is free of one or more of sulfur, phosphorus and chlorine.

* * * * *